US007308303B2

(12) United States Patent
Whitehurst et al.

(10) Patent No.: US 7,308,303 B2
(45) Date of Patent: Dec. 11, 2007

(54) THROMBOLYSIS AND CHRONIC ANTICOAGULATION THERAPY

(75) Inventors: Todd K Whitehurst, Frazier Park, CA (US); Kelly H McClure, Simi Valley, CA (US); James R Thacker, Eureka, MO (US)

(73) Assignee: Advanced Bionics Corporation, Valencia, CA (US)

( * ) Notice: Subject to any disclaimer, the term of this patent is extended or adjusted under 35 U.S.C. 154(b) by 526 days.

(21) Appl. No.: 10/285,803

(22) Filed: Nov. 1, 2002

(65) Prior Publication Data

US 2003/0083698 A1  May 1, 2003

Related U.S. Application Data

(60) Provisional application No. 60/340,076, filed on Nov. 1, 2001.

(51) Int. Cl.
*A61N 1/00* (2006.01)
*A61M 5/00* (2006.01)
(52) U.S. Cl. ........................................................ 607/3
(58) Field of Classification Search .................... 607/3, 607/9; 604/890.1, 891.1, 892.2
See application file for complete search history.

(56) References Cited

U.S. PATENT DOCUMENTS

| 3,598,111 | A | 8/1971 | Kahn et al. | |
|---|---|---|---|---|
| 4,000,972 | A | 1/1977 | Braun et al. | |
| 4,080,966 | A | 3/1978 | McNally et al. | |
| 4,232,679 | A | 11/1980 | Schulman | 607/33 |
| 4,373,527 | A | 2/1983 | Fischell | |
| 4,408,608 | A | 10/1983 | Daly et al. | 607/57 |
| 4,481,950 | A | 11/1984 | Duggan | 607/29 |

(Continued)

FOREIGN PATENT DOCUMENTS

WO    WO98/37926    9/1998

(Continued)

OTHER PUBLICATIONS

Atrial Fibrillation Investigators (AFI), "The Efficacy of Aspirin in Patients with Atrial Fibrillation. Analysis of Pooled Data From 3 Randomized Trials", Arch Intern Med, vol. 157, (1997), pp. 1237-1240.

(Continued)

*Primary Examiner*—Kristen D. Mullen
(74) *Attorney, Agent, or Firm*—Travis K. Laird; AdvantEdge Law Group, LLC

(57) ABSTRACT

Thrombolytic and/or anticoagulation therapy of the present invention includes implantation of the discharge portion(s) of a catheter and, optionally, one or more electrodes on a lead, adjacent tissue(s) to be stimulated. Stimulation pulses, i.e., drug infusion pulses and optional electrical pulses, are supplied by a stimulator implanted remotely, and through the catheter or lead, which is tunneled subcutaneously between the stimulator and stimulation site. Stimulation sites include the coronary arteries, coronary veins, cerebral arteries, other blood vessels, chambers of the heart, mesenteric vessels, deep vessels of the leg, and other locations. Disclosed treatments include drugs used for chronic treatment and/or prevention of thromboembolic disease, for acute treatment of thromboembolic disease, for acute treatment of thrombosis, and combinations of these. The invention reduces or eliminates the incidence of thromboembolic disease and related morbidities, improve symptoms resulting from thromboembolic disease, and improve patient quality of life.

24 Claims, 5 Drawing Sheets

U.S. PATENT DOCUMENTS

| | | | |
|---|---|---|---|
| 4,608,985 A | 9/1986 | Crish et al. ............... 607/74 | |
| 4,628,942 A | 12/1986 | Sweeney et al. ............ 607/118 | |
| 4,649,936 A | 3/1987 | Ungar et al. ............... 607/118 | |
| 4,793,353 A | 12/1988 | Borkan ..................... 607/60 | |
| 4,794,934 A | 1/1989 | Motoyama et al. | |
| 4,922,926 A | 5/1990 | Hirschberg et al. | |
| 4,998,535 A | 3/1991 | Selker et al. | |
| 5,011,472 A | 4/1991 | Aebischer et al. | |
| 5,078,680 A | 1/1992 | Sarnoff | |
| 5,103,821 A | 4/1992 | King | |
| 5,104,859 A | 4/1992 | Sollevi | |
| 5,109,850 A | 5/1992 | Blanco et al. | |
| 5,139,028 A | 8/1992 | Steinhaus et al. | |
| 5,151,268 A | 9/1992 | Bang et al. | |
| 5,193,539 A | 3/1993 | Schulman et al. | |
| 5,193,540 A | 3/1993 | Schulman et al. | |
| 5,199,428 A | 4/1993 | Obel et al. | |
| 5,217,022 A | 6/1993 | Nathanielsz | |
| 5,234,404 A | 8/1993 | Tuttle et al. | |
| 5,246,008 A | 9/1993 | Mueller | |
| 5,282,840 A | 2/1994 | Hudrlik | |
| 5,305,745 A * | 4/1994 | Zacouto ................... 600/324 | |
| 5,312,439 A | 5/1994 | Loeb | |
| 5,314,458 A | 5/1994 | Najafi et al. ............... 607/116 | |
| 5,324,316 A | 6/1994 | Schulman et al. | |
| 5,326,706 A | 7/1994 | Yland et al. | |
| 5,338,662 A | 8/1994 | Sadri | |
| 5,358,514 A | 10/1994 | Schulman et al. ............ 607/61 | |
| 5,405,367 A | 4/1995 | Schulman et al. | |
| 5,409,009 A | 4/1995 | Olson | |
| 5,447,529 A | 9/1995 | Marchlinski et al. | |
| 5,474,552 A | 12/1995 | Palti | |
| 5,494,822 A | 2/1996 | Sadri | |
| 5,513,644 A | 5/1996 | McClure et al. | |
| 5,549,650 A | 8/1996 | Bornzin et al. | |
| 5,551,427 A | 9/1996 | Altman | |
| 5,562,721 A | 10/1996 | Marchlinski et al. | |
| 5,634,899 A | 6/1997 | Shapland et al. | |
| 5,697,899 A | 12/1997 | Hillman et al. | |
| 5,716,318 A * | 2/1998 | Manning ................... 600/16 | |
| 5,716,937 A | 2/1998 | Haupert | |
| 5,725,563 A | 3/1998 | Klotz | |
| 5,753,517 A | 5/1998 | Brooks et al. | |
| 5,755,750 A | 5/1998 | Petruska et al. ............. 607/75 | |
| 5,759,536 A | 6/1998 | Bellgrau et al. | |
| 5,824,029 A | 10/1998 | Weijand et al. | |
| 5,840,059 A | 11/1998 | March et al. | |
| 5,865,787 A | 2/1999 | Shapland et al. | |
| 5,895,416 A | 4/1999 | Barreras et al. ............. 607/62 | |
| 5,910,484 A | 6/1999 | Haupert et al. | |
| 5,916,154 A | 6/1999 | Hobbs et al. | |
| 5,995,860 A | 11/1999 | Sun et al. | |
| 6,017,318 A | 1/2000 | Gauthier et al. | |
| 6,051,017 A | 4/2000 | Loeb et al. | |
| 6,058,331 A | 5/2000 | King | |
| 6,073,048 A | 6/2000 | Kieval et al. | |
| 6,112,116 A * | 8/2000 | Fischell et al. ............. 600/517 | |
| 6,122,544 A | 9/2000 | Organ | |
| 6,154,678 A | 11/2000 | Lauro ..................... 607/115 | |
| 6,178,349 B1 | 1/2001 | Kieval | |
| 6,183,412 B1 | 2/2001 | Benkowski et al. | |
| 6,198,965 B1 | 3/2001 | Penner et al. | |
| 6,205,359 B1 | 3/2001 | Boveja .................... 607/45 | |
| 6,206,914 B1 | 3/2001 | Soykan et al. | |
| 6,216,045 B1 | 4/2001 | Black et al. ............... 607/122 | |
| 6,228,844 B1 | 5/2001 | Wolff et al. | |
| 6,266,564 B1 | 7/2001 | Hill et al. ................. 607/9 | |
| 6,341,236 B1 | 1/2002 | Osorio et al. ............... 607/45 | |
| 6,347,247 B1 * | 2/2002 | Dev et al. ................. 607/2 | |
| 6,355,243 B1 | 3/2002 | Novokhatny et al. | |
| 6,356,777 B1 | 3/2002 | Garfield et al. | |
| 6,358,247 B1 | 3/2002 | Altman et al. | |
| 6,447,443 B1 | 9/2002 | Keogh et al. | |
| 6,464,687 B1 | 10/2002 | Ishikawa et al. | |
| 6,526,318 B1 | 2/2003 | Ansarinia ................. 607/46 | |
| 6,571,127 B1 | 5/2003 | Ben-Haim et al. | |
| 6,650,943 B1 | 11/2003 | Whitehurst et al. | |
| 6,712,753 B2 | 3/2004 | Manne ..................... 600/9 | |
| 6,845,267 B2 | 1/2005 | Harrison et al. | |
| 6,907,295 B2 | 6/2005 | Gross et al. ............... 607/118 | |
| 6,928,320 B2 | 8/2005 | King ...................... 607/5 | |
| 6,970,741 B1 | 11/2005 | Whitehurst et al. | |
| 2001/0003799 A1 | 6/2001 | Boveja .................... 607/45 | |
| 2001/0044619 A1 | 11/2001 | Altman | |
| 2002/0010492 A1 | 1/2002 | Donovan et al. | |
| 2002/0016615 A1 * | 2/2002 | Dev et al. ................. 607/2 | |
| 2002/0022873 A1 | 2/2002 | Erickson et al. ............ 607/117 | |
| 2003/0036773 A1 | 2/2003 | Whitehurst et al. | |
| 2003/0236557 A1 | 12/2003 | Whitehurst et al. | |
| 2003/0236558 A1 | 12/2003 | Whitehurst et al. | |
| 2004/0015204 A1 | 1/2004 | Whitehurst et al. | |
| 2004/0172089 A1 | 9/2004 | Whitehurst et al. ........... 607/45 | |
| 2005/0101878 A1 | 5/2005 | Daly et al. ................ 600/559 | |

FOREIGN PATENT DOCUMENTS

| | | |
|---|---|---|
| WO | WO98/43700 | 10/1998 |
| WO | WO98/43701 | 10/1998 |
| WO | 01/26729 | 4/2001 |

OTHER PUBLICATIONS

Atrial Fibrillation Investigators (AFI), "Bleeding During Antithrombotic Therapy in Patients with Atrial Fibrillation", Arch Intern Med, vol. 156, (1996), pp. 409-416.

Atrial Fibrillation Investigators (AFI), "Risk Factors for Stroke and Efficacy of Antithrombotic Therapy in Atrial Fibrillation. An Analysis of Pooled Data from Five Randomized Controlled Trials", Arch Intern Med, vol. 154, (1994), pp. 1449-1457.

Blanchard, et al., "Immunoassays of Human Prothrombin Species which Correlate with Functional Coagulant Activities", J Lab Clin Med, vol. 101, (1983), pp. 242-255.

Hassett, "Heparin Monitoring", Transfusion Medicine Update, Feb. 1996, 3 pages.

Hirsh, "Heparin", N Engl J Med, vol. 324, (1991), pp. 1565-1574.

Horton, et al., "Warfarin Therapy: Evolving Strategies in Anticoagulation", American Family Physician, (Feb. 1, 1999), pp. 635-646.

Le, et al., "The International Normalized Ratio (INR) for Monitoring Warfarin Therapy: Reliability and Relation to Other Monitoring Methods", Annals of Internal Medicine, vol. 120, (Apr. 1, 1994), pp. 552-558.

National Institute of Neurological Disorders and Stroke (NINDS) rt-PA Stroke Study Group. "Tissue Plasminogen Activator for Acute Ischemic Stroke", N Eng J Med, vol. 333, (1995), pp. 1581-1587.

Owen, et al., *The Diagnosis of Bleeding Disorders*, Little Brown and Company, Boston, (1975), pp. 109-110.

Pepke-Zaba, et al., "Validation of Impedance Cardiography Measurements of Cardiac Output During Limited Exercise in Heart Transplant Recipients", Transpl Int, vol. 3(2), (Jul. 1990), pp. 108-112.

Zivelin, et al., "Mechanism of the Anticoagulant Effect of Warfarin as Evaluated in Rabbits by Selective Depression of Individual Procoagulant Vitamin K-Dependent Clotting Factors", J Clin Invest, vol. 92, (1993), pp. 2131-2140.

Asahara, et al., "Local Delivery of Vascular Endothelial Growth Factor Accelerates Re-Endothelialization and Attenuates Intimal Hyperplasia in Balloon-Injured Rat Carotid Artery", Circulation, vol. 91, (1995), pp. 2793-2801.

Cameron, et al., "Micromodular Implants to Provide Electrical Stimulation of Paralyzed Muscles and Limbs", IEEE Transactions on Biomedical Engineering, vol. 44, No. 9, (Sep. 1997), pp. 781-790.

Erhard, et al., "Measuring Impedance for Evaluating Ischemia Damage to the Human Liver in Preparation for Transplantation", Langenbecks Arch Chir, vol. 378(4), (1993), pp. 233-238.

Gerhausser, et al., "Diagnosis of Rejection After Kidney Transplantation by Impedance Spectroscopy with an Implantable System", Biomed Tech (Berlin), 42 Suppl, (1997), pp. 160-161.

Gersing, et al., "Measuring Electric Impedance of Organs—Methodologic Principles", Biomed Tech (Berlin), vol. 36(4), (1991), pp. 70-77.

Grauhan, et al., "Electric Myocardial Impedance Registration in Humoral Rejection After Heart Tranplantation", J Heart Lung Transplant, vol. 15(2), (Feb. 1996), pp. 136-143.

Guimaraes et al. "Vascular adrenoceptors: an update" Pharmacol Rev. 2001 Jun;53(2):319-56.

Hammer et al., "Differential Inhibition of Functional Dilation of Small arterioles by indomethacin and glibenclamide" *Hypertension* 371(2):599-603 (2001).

Harms, et al., "Telemetric Assessment of Liver Impedance: Evaluation of a Device for the Noninvasive Diagnosis of Acute Rejection After Experimental Liver Transplantation", Biomed Tech (Berlin), vol. 45(3), (2000), pp. 43-50.

Hortobagyi et al., "Randomized trial of high-dose chemotherapy and blood cell autografts for high-risk primary breast carcinoma" *J. Natl. Cancer Inst*. 92:225-233 (2000).

Ishikawa, et al., "Detection of Myocardial Ischemic Injury During Simple Cold Storage by Measurement of Myocardial Electrical Impedance", J Cardiovasc Surg (Torino), vol. 37(3), (Jun. 1996), pp. 261-267.

Klagsburn, M., "The Fibroblast Growth Factor Family: Structural and Biological Properties", Progress in Growth Factor Research, vol. 1, (1989), pp. 207-235.

Lopez, et al., "VEGF Administration in Chronic Myocardial Ischemia in Pigs", Cardiovasc Res, vol. 40(2), (Nov. 1998), pp. 272-281.

Pfitzmann, et al., "Intramyocardial Impedance Measurements for Diagnosis of Acute Cardiac Allograft Rejection", Annals of Thoracic Surgery, vol. 70(2), (Aug. 2000), pp. 527-532.

Sollinger, HW., "Mycophenolate Mofetil for the Prevention of Acute Rejection in Primary Cadaveric Renal Allograft Recipients", Transplantation, vol. 60, (1995), pp. 225-232.

Unger, et al., "Basic Fibroblast Growth Factor Enhances Myocardial Collateral Flow in Canine Model", American Journal of Physiology, vol. 266, (1994), pp. H1588-1595.

Vincenti, et al., "Interleukin-2-Receptor Blockade with Daclizumab to Prevent Acute Rejection in Renal Transplantation", N Engl J Med, vol. 338, (1998), pp. 161-165.

\* cited by examiner

THROMBOLYSIS AND CHRONIC ANTICOAGULATION THERAPY

The present application claims the benefit of U.S. Provisional Patent Application Ser. No. 60/340,076, filed Nov. 1, 2001, which application is incorporated herein by reference in its entirety.

FIELD OF THE INVENTION

The present invention generally relates to implantable stimulator systems and methods for their use, and more particularly to methods utilizing one or more implantable stimulator systems for thrombolysis and chronic anticoagulation therapy.

BACKGROUND OF THE INVENTION

Thrombolytic Therapy

Thrombolytic therapy is used to dissolve blood clots (i.e., thrombi). Thrombolytic agents include protein catalysts that activate a plasma proenzyme known as plasminogen to, in turn, produce the active enzyme plasmin. Plasmin then solubilizes fibrin and degrades a number of other plasma proteins, most notably fibrinogen and the procoagulant factors V and VIII. Available thrombolytic agents include urokinase, tissue plasminogen activator (tPA), duteplase (a type of tPA), alteplase (a.k.a. activase, a type of tPA), streptokinase, anistreplase (also known as anisoylated plasminogen-streptokinase activator complex, or APSAC), and tenecteplase (a.k.a. TNKase, a type of tPA).

Indications for thrombolytic therapy include acute myocardial infarction, acute ischemic stroke, acute pulmonary embolism, acute deep venous thrombosis, and a clotted arteriovenous (AV) fistula or shunt. Bleeding is the major complication of thrombolytic therapy. Consequently, absolute contraindications include dissecting aortic aneurysm, pericarditis, hemorrhagic stroke, or neurosurgical procedures within six months or known intracranial neoplasm. Relative contraindications include major surgery or bleeding within six weeks, known bleeding diathesis, and severe uncontrolled hypertension. Streptokinase and anistreplase are potentially allergenic, so patients are usually prophylactically pre-treated with intravenous hydrocortisone.

Studies show that thrombolytic therapy administered within 24 hours of an acute myocardial infarction leads to decreased mortality and morbidity. Of the 900,000 people who have heart attacks in the United States every year, only one-fifth receive thrombolytic drugs of any kind and only one-tenth receive tPA. Streptokinase, an effective clot buster sold at one tenth the price of tPA, is a popular rival of tPA.

A 1995 study showed that, for every 100 carefully selected patients with ischemic stroke and no CT evidence of intracranial hemorrhage treated with tPA within three hours after stroke onset, an additional 12 recover without residual disability. Some evidence suggests that the earlier this therapy is delivered, the more likely the patient is to recover neurological function.

Anticoagulation Therapy

Chronic anticoagulation therapy is used to prevent blood clots, e.g., in patients with a history of thromboembolism formation. The disorders treated with chronic anticoagulation therapy include acute venous thrombosis (e.g., deep venous thrombosis or DVT) or pulmonary embolism. (DVT usually refers to a blood clot in a deep vein of a limb, most commonly one of the legs.) Chronic anticoagulation therapy may also be used to prevent arterial thromboembolism associated with atrial fibrillation, left ventricular thrombus, and other disorders that have demonstrated a significant risk of thromboembolism (e.g., presence of lupus anticoagulant antibody and/or anti-cardiolipin antibody, and paradoxical embolism).

Chronic anticoagulation therapy is also used for prophylaxis of thromboembolism in asymptomatic patients with no history of thrombosis but with a disorder(s) or other risk factor(s) for forming a thromboembolism. Such disorders include chronic or paroxysmal atrial fibrillation, presence of a mechanical cardiac valve, post-operative venous thrombosis, post-myocardial infarction, cardiomyopathy, documented procoagulant disorder with first degree relative with DVT, and presence of a central venous catheter. Chronic anticoagulation therapy may also be used for prophylaxis of thromboembolism during chemotherapy in women with breast cancer.

Cardiovascular Disease

According to 1997 estimates, 60 million Americans have one or more forms of cardiovascular disease. Coronary heart disease affects approximately 12.2 million Americans, with 6.3 million afflicted with angina pectoris. An estimated 7.7 million Americans have suffered a myocardial infarction, and an additional 4.4 million have suffered a stroke. Many of these patients are on chronic anticoagulation therapy. A few were fortunate enough to receive thrombolytic therapy within a few hours following a myocardial infarction or a stroke.

Atrial Fibrillation

Atrial fibrillation (AF), the most commonly encountered arrhythmia in clinical practice, causes significant morbidity and mortality in affected individuals and is a considerable burden on healthcare services. Clinical manifestations range from palpitations through heart failure to cerebral embolism and ischemic stroke. AF is present in 17 to 25% of acute stroke patients and is estimated to increase stroke risk five-fold compared with patients in sinus rhythm.

Studies show that aspirin therapy has a modest benefit, reducing stroke rate by one-fifth, whereas warfarin limits annual incidence of stroke to 1.4%. Such anticoagulant therapy, however, can cause major hemorrhage at a rate of 2.3% per year.

The true prevalence of AF is difficult to establish, but is probably between 0.4 and 1.7% of the adult population, with approximately 20 to 30% of cases displaying a paroxysmal pattern. Community-based studies have demonstrated a male predominance and a striking relationship with increasing age—the prevalence rising from less than 1% at younger than 65 years, 2.3% at 65 to 69 years, 4.1% at 70 to 74 years, 5.8% at 75 to 79 years, 6.4% at 80 to 84 years, and 8.1% at older than 85 years of age. It has been estimated that there are 2.2 million cases of AF in the United States, with a median age of 75 years. Thus, AF is a common condition in the elderly and will only increase as the mean population age rises.

Deep Vein Thrombosis (DVT) and Pulmonary Embolism

Deep venous thrombosis (DVT) is a relatively common disease that is often encountered by family physicians. Epidemiologic data suggest that the annual incidence of a first episode of DVT ranges from 60 to 180 cases per 100,000 people, or more than 300,000 new cases annually in the United States. The cost burden of this disease is quite high, since most patients with DVT require one or more diagnostic tests, treatment with intravenous heparin, and a three- to seven-day hospital stay.

DVT is development of a thrombus of fibrin, red blood cells, platelets, and granulocytes within a deep vein. Thrombi form where blood flow is stagnant and where eddies form along the cusps of valves. The danger lies in pulmonary embolization through thrombus detachment. The embolus floats through veins of increasing diameter to the right side of the heart, where it is pumped to the pulmonary arterial system in the lungs; the embolus lodges where its diameter is greater than the lumen of the artery.

An estimated 500,000 people in the United States will suffer from some degree of pulmonary emboli (PE) this year, and 50,000 will die as a result. Not all PEs are life-threatening; in fact, many people unknowingly have had one or more PEs. The outcome of any PE depends largely on the length, diameter, and number of emboli carried to the lungs. Large emboli are usually 1.0 to 1.5 cm in diameter and can commonly be 5 cm long. The origin of most major PE is the ilio-femoral veins, with relatively fewer coming from the calf veins and the inferior vena cava.

Paradoxical Embolism

Paradoxical embolism is the passage of a clot (thrombus) from a vein to an artery. As described above, when clots in veins break off (embolize), they travel to the right side of the heart and then, normally, to the lungs, where they lodge. The lungs prevent clots from entering the arterial circulation. However, when there is a hole in the wall between the two upper chambers of the heart (an atrial septal defect), a clot can cross from the right to the left side of the heart, then into the arteries as a paradoxical embolism. Once in the arterial circulation, a clot can travel to the brain, block a vessel there, and cause a stroke (cerebrovascular accident). Because of this risk of stroke from paradoxical embolism, even small atrial septal defects are usually repaired.

Warfarin (Coumadin®)

Warfarin is the most frequently prescribed oral anticoagulant, the fourth most prescribed cardiovascular agent, and the overall eleventh most prescribed drug in the United States, with annual sales of approximately $500 million. Nonetheless, in 1995, the Agency for Healthcare Policy and Research (AHCPR) reported that warfarin is greatly underutilized for stroke prevention.

Warfarin is an antagonist of vitamin K, a necessary element in the synthesis of clotting factors II, VII, IX and X, as well as the naturally occurring endogenous anticoagulant proteins C and S. These factors and proteins are biologically inactive without the carboxylation of certain glutamic acid residues. This carboxylation process requires oxidized vitamin K as a cofactor and occurs primarily in the liver. Antagonism of vitamin K or a deficiency of this vitamin reduces the rate at which these factors and proteins are produced, thereby creating a state of anticoagulation.

Therapeutic doses of warfarin reduce the production of functional vitamin K-dependent clotting factors by approximately 30 to 50 percent. A concomitant reduction in the carboxylation of secreted clotting factors yields a 10 to 40 percent decrease in the biologic activity of the clotting factors. As a result, the coagulation system becomes functionally deficient.

Warfarin prolongs the prothrombin time (PT), which is responsive to depression of three of the four vitamin K-dependent coagulation factors (factors II, VII, and X). The International Normalized Ratio (INR) has been developed and adopted as a method to standardize monitoring of oral anticoagulant therapy. The INR is less reliable as a measure of anticoagulation in the early course of warfarin therapy; however, it is more reliable than the PT or PT ratio for clinical management.

Warfarin does not affect established thrombus and does not reverse ischemic tissue damage. Warfarin therapy prevents further extension of the clot and prevents secondary thromboembolic complications.

Heparin

Heparin is a parenteral anticoagulant widely used in clinical medicine. Compared with low molecular weight heparins, unfractionated heparin produces a less predictable anticoagulant response due primarily to its reduced bioavailability after subcutaneous administration of low doses, its dose-dependent clearance, and differences among patients in the nonspecific binding of heparin to proteins and cells.

Heparin exerts its anticoagulant action by accelerating the activity of antithrombin III (ATIII). The interaction of heparin with ATIII produces a conformational change in ATIII, which accelerates the ability of ATIII to inactivate the coagulation enzymes thrombin (factor IIa), factor Xa, and factor IXa.

The activated partial thromboplastin time (APTT) is usually used to monitor heparin therapy since it is sensitive to the inhibitory effects of heparin on thrombin, factor Xa, and factor IXa. High doses of heparin interfere with platelet aggregation, which, in turn, prolongs bleeding time, although typical doses of heparin do not affect bleeding time.

Heparin does not lyse existing clots. It is important to achieve therapeutic heparin concentrations quickly following a pathological thrombus in order to prevent clot extension.

Prothrombin Time (PT) and International Normalized Ratio (INR) Measurement

The prothrombin time (PT) test essentially monitors the time it takes for a sample of blood to clot after the blood is exposed to a coagulation-promoting agent (thromboplastin). The result of a test is expressed as an International Normalized Ratio (INR), which was developed to reduce variability in PT test results. In order to make PT times comparable across labs, the World Health Organization (WHO) has designated an international reference preparation (IRP) of thromboplastin (rTF/95) as a standard. This allows commercial thromboplastins to be compared to a WHO reference standard and be corrected to adjust to the WHO reference by the International Sensitivity Index (ISI). The INR is then calculated according to the following formula: INR=(Patient PT in seconds/Mean Normal PT in seconds)^ISI.

An INR of 1 typically corresponds to normal blood coagulation. Assuming an ISI of 1, an INR of 2 means that the coagulation time is about twice as long as normal, an INR of 3 equates to about three times as long as normal, and so on.

Alternative Coagulation Assays to PT

In 1994, Le, et al. investigated other coagulation assays in 79 patients attending an anticoagulation clinic. [Le, et al. "The International Normalized Ratio (INR) for Monitoring Warfarin Therapy: Reliability and Relation to Other Monitoring Methods" *Annals of Internal Medicine,* 1 Apr. 1994; 120: 552-558.] Because determinations of residual specific prothrombin activity and native prothrombin antigen have been proposed as being better techniques for monitoring oral anticoagulant therapy than the prothrombin time, the authors examined the relation between these measurements and INR values. Specifically, they evaluated the Specific Prothrombin Assay and a Native Prothrombin Antigen Assay.

Specific Prothrombin Assay (Factor II): Prothrombin activity was assayed by a one-stage assay in which a mixture of 100 μL of a prothrombin-depleted human serum/barium-adsorbed bovine plasma reagent and 100 μL of a 1:10 to 1:40 dilution of test plasma were clotted by the addition of 200 μL of a thromboplastin C reagent containing $CaCl_2$. Clotting times were converted to percent normal plasma prothrombin activity from a log-log standard curve prepared with dilutions of control pooled plasma.

Native Prothrombin Antigen Assay: The authors measured plasma native prothrombin antigen concentration with native prothrombin antigen enzyme immunoassay kits. Color was measured at 450 nm with a Thermomax enzyme-linked immunosorbent assay reader.

Relations among Values for International Normalized Ratios, Native Prothrombin Antigen, and Specific Prothrombin Activity: The authors confirmed an earlier report of good correlation between residual plasma native prothrombin antigen levels measured by enzyme immunoassay and residual specific prothrombin activity measured by a one-stage coagulation method (r=0.92, n=89). A mean INR range of 2.0 to 3.0 corresponded to between about 40% to 20% residual native plasma prothrombin.

Activated Partial Thromboplastin Time (PTT) Measurement

The intrinsic capability of blood to form a fibrin clot requires coagulation factors XII (Hageman), XI (plasma thromboplastin antecedent), IX (Christmas), VIII (anti-hemophilic), X (Stuart-Prower), V (proaccelerin), II (prothrombin), I (fibrinogen), platelet lipid, and calcium. Historically, intrinsic coagulation was measured by timing fibrin clot formation upon recalcification of citrated, anticoagulated, platelet rich plasma. Measurement with platelet rich plasma, however, relied on the platelets as a source of phospholipid to the extent that variables such as centrifugation and patient platelet count had a significant bearing on the test results. The partial thromboplastin time (PTT) introduces a platelet substitute that eliminates test variability due to the availability of platelet phospholipid. By adding a substance to activate factors XII and XI, the contact factors, the partial thromboplastin time becomes the "activated" partial thromboplastin time (APTT). Because coagulation endpoints are shorter and sharper than with the PTT, the APTT has proven to be a simple and highly reliable measurement of the intrinsic coagulation mechanism.

Laboratory monitoring of heparin therapy is desirable to ensure that an appropriate antithrombotic effect is obtained, while guarding against bleeding complications of an overdosage. Currently, the APTT is the most common test used to monitor heparin therapy. Monitoring by APTT evaluates heparin's overall activity throughout the entire coagulation system i.e., inactivation of thrombin, Xa, XIIa, XIa, and IXa. Heparin treatment is usually monitored to maintain the ratio of the patient's APTT to the mean control APTT within a defined range of approximately 1.5 to 2.5, referred to as the therapeutic range. Laboratory and clinical studies have established a therapeutic range that is equivalent to a heparin level of 0.2 to 0.4 U per milliliter (mL) by protamine titration, or 0.35 to 0.7 U per mL according to the level of anti-Xa activity. It should be noted that the responsiveness of the reagents used in APTT tests can vary widely. The therapeutic range for any given APTT reagent should therefore be established in the clinical laboratory to correspond to a heparin level of 0.2 to 0.4 U/mL by protamine titration.

Alternative Coagulation Assays to PTT

Anti-Xa Assay: An alternative approach is to assay for heparin exploiting its catalysis by antithrombin III inhibition of coagulation enzymes, particularly factor Xa. The factor Xa inhibition test (anti-Xa assay) is the most useful test for assaying the widest variety of therapeutic heparin preparations. In this method, both factor Xa and antithrombin III are present in excess and the residual factor Xa activity is inversely proportional to the heparin concentration. The assumption is made that the patient has a normal concentration of antithrombin III. (For a patient with ATIII deficiency a heparin concentration is measured, but this does not necessarily correspond to the anticoagulant capacity in vivo.) It is recommended to also measure the antithrombin III level for all patients under heparin therapy when using this type of assay to ensure normal ATIII activity. The therapeutic range of the anti-Xa assay in the treatment of thromboembolic disease established by laboratory and clinical studies for unfractionated heparin is 0.35 to 0.7 anti-Xa Units/mL. The therapeutic range for LMW heparins has not been well established at this time.

There are several clinical situations where the specific measurement of heparin levels using the anti-factor Xa method may be necessary. Patients receiving heparin but demonstrating an inadequate APTT response can be evaluated for heparin by the anti-Xa assay. Monitoring of heparin is difficult by conventional methods when the baseline APTT is prolonged as seen in patients with lupus anticoagulants and deficiencies of factor XII (Hagemen factor), prekallikrein (Fletcher factor), and high molecular weight kininogen (Fitzgerald factor). A quantitative anti-Xa assay makes heparin monitoring possible in these clinical situations.

Sensing Cardiac Function

A number of means are available for assessing cardiac function. An ultrasound echocardiogram can non-invasively assess a number of parameters of the heart, such as left ventricle size and cardiac output. An electrocardiogram (ECG) may be recorded non-invasively or invasively, and may be used to detect or diagnose a number of cardiac conditions, e.g., ischemia, arrhythmia, etc. Invasive pressure transducers may be used to determine left ventricular end diastolic pressure, pulmonary capillary wedge pressure, and systemic blood pressure. For instance, a thermal dilution catheter, the dye-dilution method, and/or catheter pressure transducers/catheter tip transducers may be used to measure blood pressure or cardiac output. Cardiac output, the total volume of blood pumped by the ventricle per minute, is the product of heart rate and stoke volume.

In a 1990 study of 21 heart transplant patients, Pepke-Zaba, et al. compared cardiac output measured by thermodilution and by impedance cardiography. They found close agreement between the measurements, both at rest and during exercise. Both measurements followed changes in heart rate and oxygen consumption. Both thermodilution and impedance cardiography methods elicited good reproducibility of cardiac output measurements at rest and during exercise. The authors concluded that the noninvasive and continuous record of cardiac output obtained by impedance cardiography can be used for the monitoring of cardiac output. [Pepke-Zaba, et al. "Validation of impedance cardiography measurements of cardiac output during limited exercise in heart transplant recipients" Transplant International, 1990 Jul;3(2):108-12.]

As should be understood by the foregoing, given the prevalence of thromboembolic disease, alternative treatments and improvements in monitoring, preventing, and treating thromboembolic disease are needed. For instance, a closed-loop system would allow automatic or semi-automatic adjustment of treatment and would allow tighter control of clotting than possible with conventional periodic tests of clotting parameters.

BRIEF SUMMARY OF THE INVENTION

The invention disclosed and claimed herein provides methods for preventing and treating thromboembolytic disease and relieving its symptoms using one or more drugs by means of a stimulator comprising an implantable pump(s) and catheter(s) and an optional implantable signal generator(s) for additionally delivering electrical stimulation. The present invention overcomes the shortfalls of all prior art treatment devices to achieve unprecedented levels of treatment by combining administration of acute (on-demand) and traditional chronic (basal or periodic bolus) treatment and prevention of thromboembolic disease. Additionally, the present invention optionally combines electrical stimulation with delivery of one or more drugs for acute and/or chronic treatment. In addition, some embodiments of the present invention include monitoring of anticoagulation status to achieve an unprecedented level of treatment of thromboembolic disease.

Anticoagulation therapy may be carried out by delivery of one or more known drugs or other substances known to decrease coagulability. Such drugs may include any and all forms of heparin, including low molecular weight heparin derivatives. Such drugs may also include any form of warfarin. Such drugs may also include any form of aspirin or any other substance known to inhibit platelet aggregation, such as clopidogrel and ticlopidine. Such substances may also include antibodies to any clotting factors or other enzymes or substances believed to be involved in the clotting process, such as those mentioned herein.

In some embodiments of the invention, anticoagulation therapy is carried out chronically through a basal rate and/or periodic bolus delivery of an anticoagulant(s). The parameters of delivery may be constant or may be modulated by a clinician, other caregiver, or the patient. The parameters of delivery may also be modulated by sensed data or by another device(s), as discussed herein.

In other embodiments of the invention, delivery of an anticoagulant(s) may be increased during an acute emergency, e.g., myocardial infarction, stroke (a.k.a., cerebrovascular accident, or CVA), evolving deep vein thrombosis, and the like. Such an increase may reflect an increase in basal rate and/or an increase in bolus dose and/or rate. This increase in delivery may be initiated by a clinician, other caregiver, or the patient. This increase in delivery may additionally or alternatively be initiated by sensed data or by another device(s), as discussed herein.

In yet other embodiments of the invention, delivery of a thrombolytic(s) may be triggered during an acute emergency, e.g., myocardial infarction, stroke, evolving deep vein thrombosis, and the like. Such delivery may be achieved through a basal rate and/or periodic bolus delivery of a thrombolytic(s). This delivery may be initiated by a clinician, other caregiver, or the patient. This delivery may additionally or alternatively be initiated by sensed data or by another device(s), as discussed herein.

The stimulator used with the present invention possesses one or more of the following properties, potentially among others:

at least one pump and at least one catheter for delivering a drug or drugs to surrounding tissue and, optionally, at least two electrodes for applying stimulating current to surrounding tissue;

electronic and/or mechanical components encapsulated in a hermetic package made from biocompatible material(s);

an electrical coil or other means of receiving energy and/or information inside the package, which receives power and/or data by inductive or radio-frequency (RF) coupling to a transmitting coil placed outside the body, thus avoiding the need for electrical leads to connect devices to a central implanted or external controller;

means for receiving and/or transmitting signals via telemetry;

means for receiving and/or storing electrical power within the stimulator; and a form factor making the stimulator implantable in a target area in the body.

A stimulator may operate independently, or in a coordinated manner with other implanted stimulators, other implanted devices, and/or with devices external to a patient's body. For instance, a stimulator may incorporate means of sensing thromboembolic disease, cardiac ischemia, cerebral ischemia, pulmonary ischemia, limb ischemia, mesenteric ischemia, myocardial infarction, stroke, pulmonary embolism, deep vein thrombosis, one or more symptoms of any of these, and/or the coagulation state of the patient. Sensed information may be used to control the drug and/or electrical stimulation parameters of the stimulator in a closed loop manner. The sensing and stimulating means may be incorporated into a single stimulator, or a sensing means may communicate sensed information to at least one stimulator with stimulating means.

For most patients, a continuous or intermittent stimulation throughout the day is needed to provide an adequate amount of treatment. These patients may best utilize a stimulator that has a self-contained power source sufficient to deliver repeated pulses for at least several days and that can be recharged repeatedly, if necessary. In accordance with the teachings of the present invention, the use of a stimulator with a rechargeable battery thus provides these patients the portability needed to free the patient from reliance on RF power delivery. Alternatively, the power source may be a primary battery that may last several years.

For purposes of this patent application, it is sufficient to note that RF controlled stimulators receive power and control signals from an extra corporeal antenna coil via inductive coupling of a modulated RF field. Battery-operated stimulators incorporate a power source within the device itself but rely on RF control, inductive linking, or the like to program stimulus sequences and, if a rechargeable/replenishable power source is used, to recharge/replenish the power source, when needed. In accordance with the present invention, each implanted stimulator may be commanded to produce an electrical and/or infusion pulse of a prescribed magnitude and duration and at a repetition rate sufficient to treat the targeted tissue.

For instance, program delivery may be directed with commands from a patient-governed control switch or controller, which may be handheld, containing a microprocessor and appropriate nonvolatile memory, such as electronically erasable programmable read-only-memory (EEPROM). The controller may control the implantable stimulator by any of various means. For instance, the stimulator may sense the proximity of a permanent magnet located in the controller, or may sense RF transmissions from the controller. However, it will be evident to those of skill in circuitry and computing that many different system architectures and components could be used to achieve similar functionality with either a battery-powered or RF-powered stimulator.

BRIEF DESCRIPTION OF THE DRAWINGS

The above and other aspects of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1A:
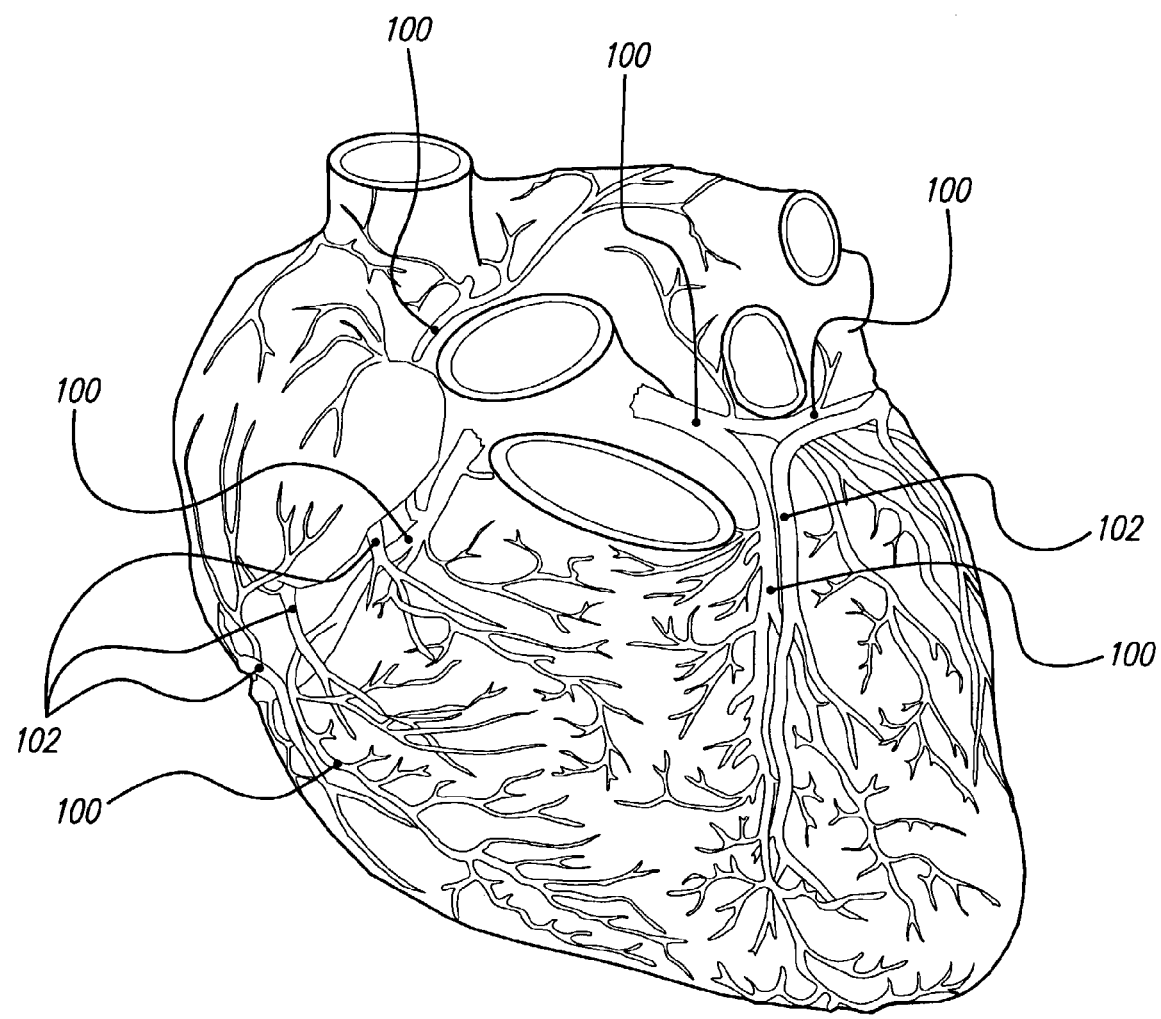
FIG. 1A is a view of the sternocostal surface of the heart.
Figure 1B:
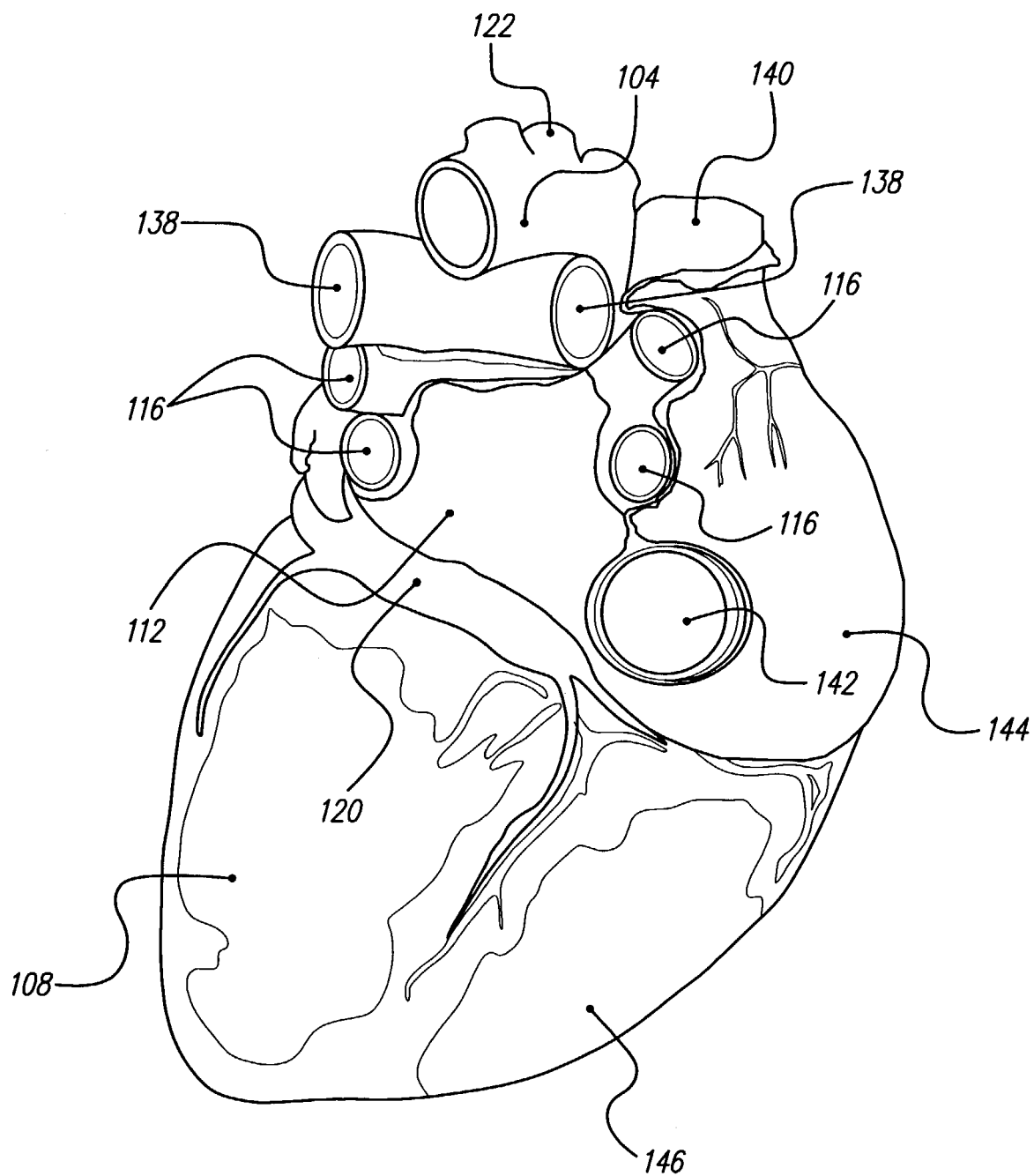
FIG. 1B is a posteroinferior view of the diaphragmatic surface of the heart.
Figure 2:
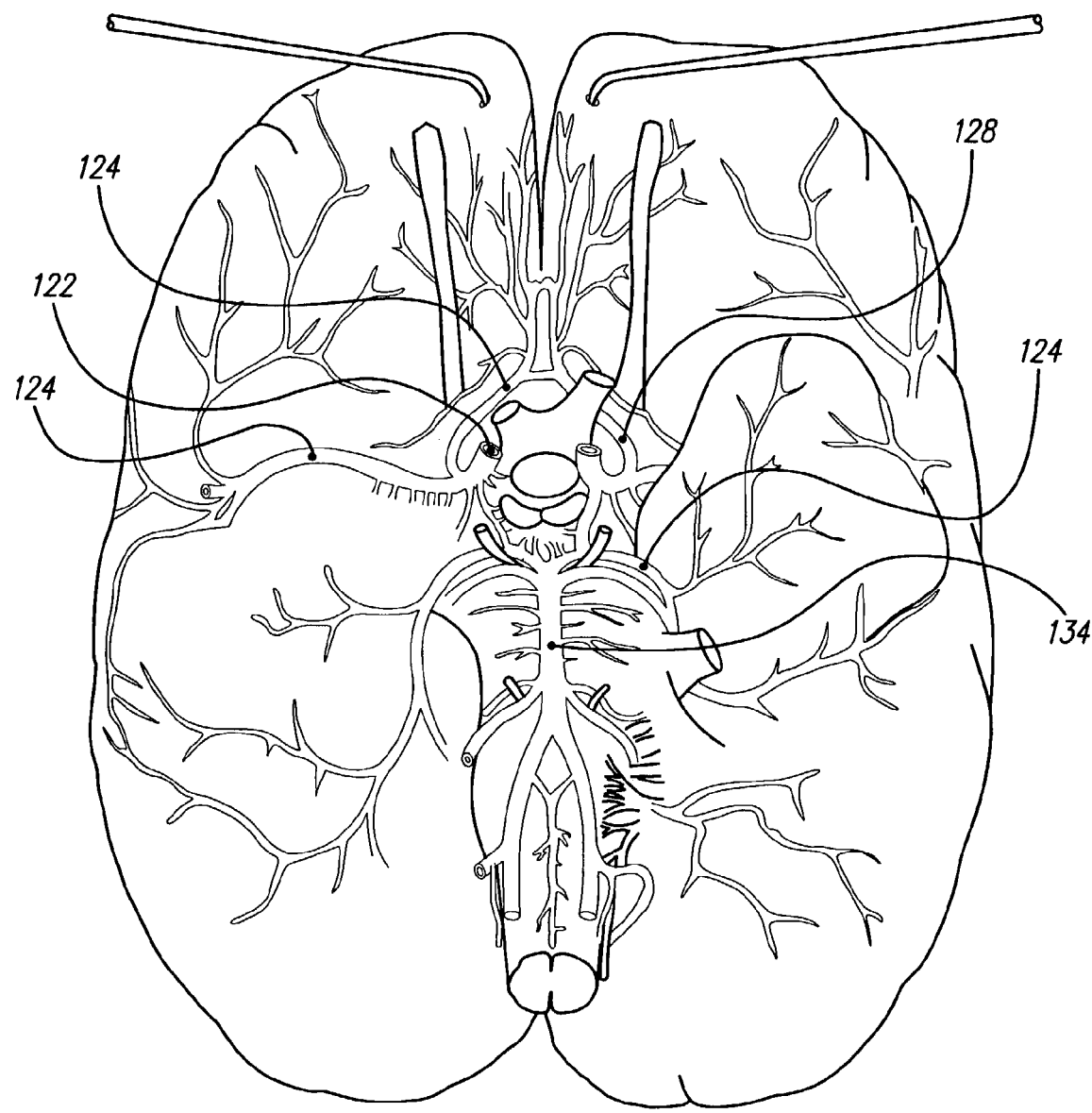
FIG. 2 is an inferior view of the arteries of the brain.

FIG. 1A depicts the coronary arteries and the cardiac veins of the sternocostal surface of the heart, while FIG. 1B is a posteroinferior view of the diaphragmatic surface of the heart, and FIG. 2 shows an inferior view of the arteries of the brain. As mentioned earlier, delivery of one or more stimulating drugs may be used to prevent or treat thromboembolic disease. Electrical stimulation may also be applied during infusion of a stimulating drug(s).

The drug(s) are preferably delivered to any vessel that may influence the coronary circulation, including one or more of the coronary arteries 100 (which herein describes also branches of the coronary arteries), one or more of the coronary veins 102 (also including branches), the aorta 104, the left ventricle 108, the left atrium 112, one or more of the pulmonary veins 116, and/or the coronary sinus 120. Such application is most appropriate for, but not limited to, patients with cardiac disease, e.g., history of myocardial infarction, coronary artery disease, or atrial fibrillation.

The drug(s) are additionally or alternatively delivered to any vessel that may influence the cerebral circulation, including any of the carotid arteries 122 (FIG. 1B shows the left common carotid artery and FIG. 2 shows the internal carotid artery), the aorta 104, any of the anterior, middle, or posterior cerebral arteries 124, the circle of Willis 128, any of meningeal arteries (not shown), and/or the basilar artery 134. Such application is most appropriate for, but not limited to, patients with history of or with risk factors for stroke.

The drug(s) are additionally or alternatively delivered to any vessel that may influence the pulmonary circulation, including any of the pulmonary arteries 138, the superior vena cava 140, the inferior vena cava 142, the right atrium 144, and the right ventricle 146. Such application is most appropriate for, but not limited to, patients with history of pulmonary embolism (PE) or with risk factors for PE.

The drug(s) are additionally or alternatively delivered to any vessel that may influence the circulation of the lower limbs, including any of the deep veins of the leg (not shown), any of the ilio-femoral vessels (not shown, e.g., common iliac vessel, internal iliac vessel, external iliac vessel, femoral vessel), and calf veins (not shown). Such application is most appropriate for, but not limited to, patients with history of deep vein thrombosis (DVT) or with risk factors for DVT.

The drug(s) are additionally or alternatively delivered to any vessel that may influence the circulation of the intestinal or other visceral organs, including any of the mesenteric vessels, renal vessels, celiac trunk, and middle colic artery (none shown). Such application is most appropriate for, but not limited to, patients with history of or with risk factors for mesenteric ischemia.

Target sites for drug infusion may additionally or alternatively include any other blood vessel, as anticoagulation therapy is typically delivered systemically. Thrombolytic therapy is ideally but not necessarily targeted to an occluded vessel, in order to avoid systemic side effects. A blood vessel that is unlikely to suffer significant trauma with implantation or attachment of a chronic infusion catheter (e.g., the inferior vena cava 142) is preferred in the case of systemic therapy. As used herein, reference to any vessel refers also to the branches of the vessel.

As indicated above, the present invention is directed to preventing and treating thromboembolytic disease and relieving its symptoms. In accordance with the teachings of the present invention, one or more stimulating drugs, possibly combined with electrical stimulation, are applied to one or more of the above mentioned areas for such treatment. As used herein, stimulate, stimulation, and stimulating refer to infusion of a stimulating drug(s) and/or supplying electrical current pulses. As such, infusion parameters and/or electrical current parameters are sometimes referred to herein as simply stimulation parameters, which parameters may include amplitude, volume, pulse width, infusion rate, and the like. Similarly, stimulation pulses may be pulses of electrical energy and/or pulses of drugs infused by various means and rates of infusion, such as intermittent infusion, infusion at a constant rate, and bolus infusion.

As used herein, stimulating drugs comprise medications and other pharmaceutical compounds, anesthetic agents, synthetic or natural hormones, neurotransmitters, interleukins, cytokines, lymphokines, chemokines, growth factors, and other intracellular and intercellular chemical signals and messengers, and the like. In addition, certain neurotransmitters, hormones, and other drugs are excitatory for some tissues, yet are inhibitory to other tissues. Therefore, where, herein, a drug is referred to as an "excitatory" drug, this means that the drug is acting in an excitatory manner, although it may act in an inhibitory manner in other circumstances and/or locations. Similarly, where an "inhibitory" drug is mentioned, this drug is acting in an inhibitory manner, although in other circumstances and/or locations, it may be an "excitatory" drug. In addition, stimulation of an area herein includes stimulation of cell bodies and axons in the area.

According to the present invention, an implantable pump and catheter(s) are used to deliver one or more stimulating drugs, plus, optionally, an implantable signal generator and electrode(s) may also deliver electrical stimulation to the target area(s). One or more catheters are surgically implanted to infuse the stimulating drug(s), and, optionally, electrode(s) on a lead(s) are implanted to provide electrical stimulation.

The invention includes at least one stimulator. In the case of drug infusion only, a preferred stimulator comprises an implantable pump. In the case of electrical stimulation, as well, a preferred stimulator also comprises an implantable pulse/signal generator (IPG). In cases where both electrical stimulation and drug infusion are required or desired, more than one stimulators may be used. Alternatively, a stimulator may provide both electrical stimulation and one or more stimulating drugs.

The present invention includes a stimulator that may be implanted in a surgically-created shallow depression or opening, e.g., in the thorax, abdomen, or above the buttock. The stimulator preferably conforms to the profile of surrounding tissue and/or bone, and is compact. This may minimize any cosmetic impact, and minimize pressure applied to the skin, which pressure can result in skin erosion or infection. As such, a stimulator of certain embodiments of the present invention has a diameter of about 75 mm, or only about 65 mm, or even less than about 55 mm. In these configurations, stimulator thickness may be approximately 10-12 mm, or even less than about 10 mm.

Figure 3:
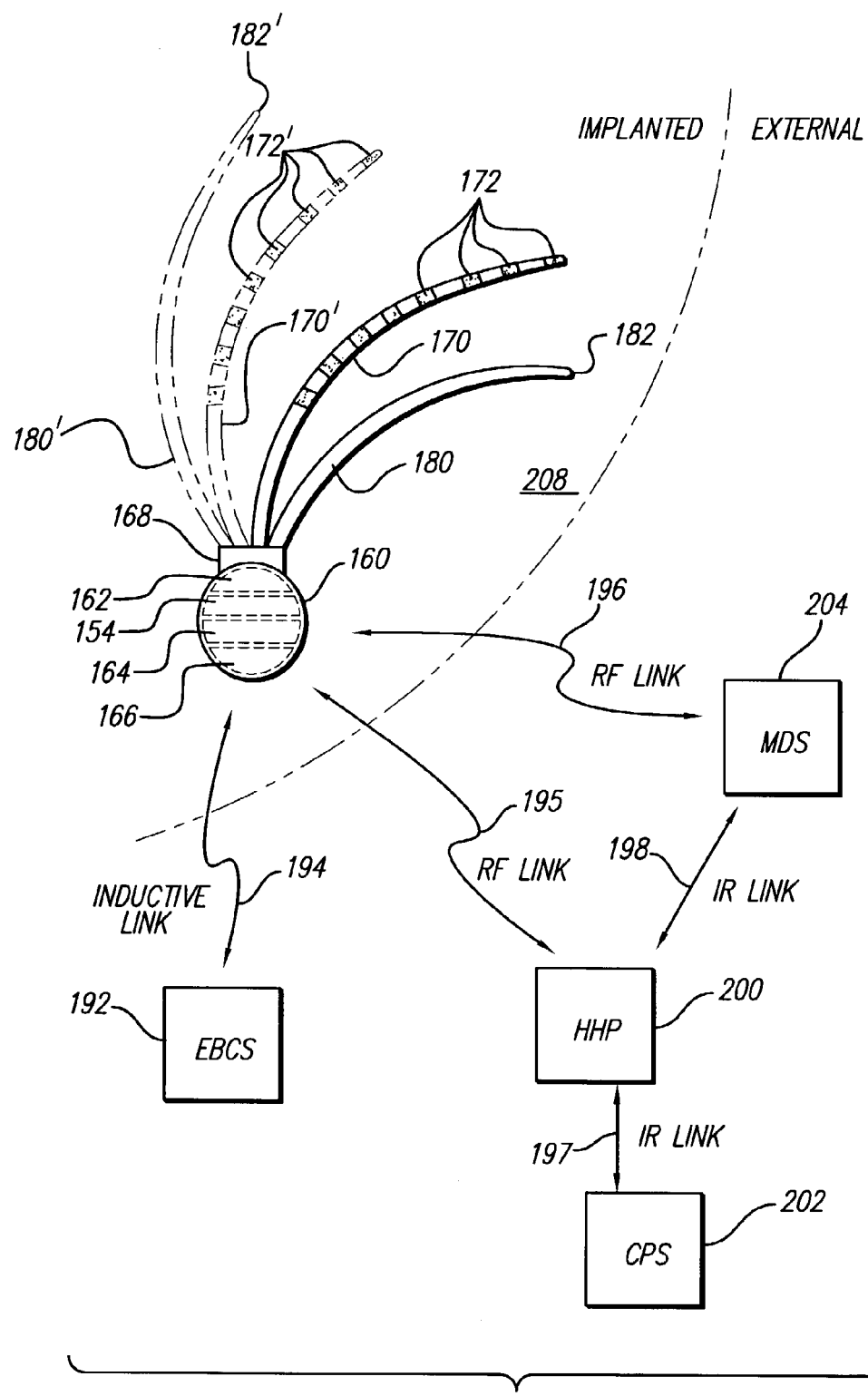
FIG. 3 illustrates an exemplary embodiment of a stimulation system of the present invention and exemplary external components of the invention.

In one preferred embodiment seen in FIG. 3, one or more catheters 180 and, optionally, one or more leads 170 attach to stimulator 160 and run subcutaneously, such as in a surgically-created tunnel(s), to the tissues to be stimulated. In the case of treatment including electrical stimulation, one or more electrodes 172 are carried on lead 170 having a proximal end coupled to stimulator 160. Electrode(s) 172 may include, for instance, a tip electrode and/or one or more ring electrodes, allowing, e.g., temporally synchronized stimulation. The lead contains wires electrically connecting electrodes 172 to stimulator 160. Stimulator 160 contains electrical components 154 that produce electrical stimulation pulses that travel through the wires of lead 170 and are delivered to electrode(s) 172, and thus to the tissue surrounding electrode(s) 172. Implantation of such stimulators, leads, and catheters in the locations specified herein is performed as known to those in the art, e.g., as known to interventional cardiologists.

In the case of treatment alternatively or additionally constituting drug infusion, catheter(s) 180 are coupled at a proximal end to stimulator 160, which contains at least one pump 162 for storing and dispensing one or more drug(s) through the catheter(s) 180. At or along a distal end, catheter 180 has at least one discharge portion 182 for infusing dosages of one or more drugs into a predetermined site. Catheter 180 may also act as a lead, additionally including electrode(s) 172 at and/or along its distal end.

To protect the components inside stimulator 160, some or all of the case of the stimulator may be hermetically sealed. For additional protection against, e.g., impact, the case may be made of metal (e.g. titanium), ceramic, or the like, which materials are also, advantageously, biocompatible. The material comprising the case of the stimulator 160 may be chosen to limit passage of water vapor, while permitting passage of electromagnetic fields used to transmit data and/or power. In addition, stimulator 160 may be configured to be Magnetic Resonance Imaging (MRI) compatible.

According to embodiments as depicted in FIG. 3, at least one lead 170 and/or catheter 180 is attached to stimulator 160, via a suitable connector(s) 168, if necessary. Each lead includes at least one electrode 172, and may include as many as sixteen or more electrodes 172. As known in the art, the case of stimulator 160 (a.k.a. the can) may act as an indifferent electrode for monopolar stimulation. Additional leads 170' and/or catheter(s) 180' may be attached to stimulator 160. Hence, FIG. 3 shows (in phantom lines) a second catheter 180', having discharge portion 182', and a second lead 170', having electrodes 172' thereon, also attached to stimulator 160.

Lead(s) 170/170' may, for instance, be less than about 5 mm in diameter, or may be even less than about 1.5 mm in diameter. Electrodes 172, 172' may be made of a noble or refractory metal or compound, such as platinum, iridium, tantalum, titanium, titanium nitride, niobium, or alloys of any of these, in order to avoid corrosion or electrolysis which could damage the surrounding tissues and/or the device. In certain embodiments, stimulator 160 is programmable to produce monopolar electrical stimulation, e.g., using the stimulator case as an indifferent electrode, or bipolar electrical stimulation, e.g., using one of the electrodes of the electrode array as an indifferent electrode. For instance, stimulator 160 may have at least four channels and may drive up to sixteen electrodes or more.

Stimulator 160 (which herein refers to implantable pump stimulators, IPG/pump combination stimulators, and/or other alternative devices known in the art) contains, when necessary and/or desired, electrical circuitry 154 (FIG. 3) for receiving data and/or power from outside the body by inductive, radio frequency (RF), or other electromagnetic coupling. In some embodiments, electrical circuitry 154 includes an inductive coil for receiving and transmitting RF data and/or power, an integrated circuit (IC) chip for decoding and storing stimulation parameters and generating stimulation pulses (either intermittent or continuous), and additional discrete components required to complete the circuit functions, e.g., capacitor(s), resistor(s), coil(s), and the like. Circuitry 154 may dictate, for instance, the amplitude and duration of the electrical current pulse, when electrical stimulation is used.

Stimulator 160 may also advantageously include a programmable memory 164 for storing set(s) of data, stimulation, and control parameters. Among other things, memory 164 may allow electrical and/or drug stimulation and/or control parameters to be adjusted to settings that are safe and efficacious with minimal discomfort for each individual. Specific parameters may provide therapeutic advantages for various types and degrees of thromboembolic disease. For instance, some patients may respond favorably to intermittent stimulation, while others may require continuous stimulation for treatment and relief. Different medications, infusion parameters, and/or electrical stimulation parameters may have different effects on anticoagulation and thrombolysis. In some embodiments, electrical and drug stimulation parameters are controlled independently, e.g., continuous drug stimulation and no electrical stimulation. However, in some instances, they are advantageously coupled, e.g., electrical stimulation may be programmed to occur only during drug infusion.

Electrical stimulation may be applied as for cardiac pacing and/or cardiac defibrillation. Such stimulation is commonly performed by implantable devices referred to as cardiac pacemakers (used to treat cardiac arrhythmias or other cardiac disease) and implantable cardiac defibrillators (ICDs, used to treat cardiac fibrillation), respectively. Modern ICDs perform both the pacing and defibrillating functions. Operation of these devices, including stimulation parameters, are well-known to those skilled in the art.

In addition, different parameters may have different effects on different tissue. Therefore, stimulation and control parameters may be chosen to target specific neural, muscular, and/or other cell populations and to exclude others, or to increase activity in specific neural, muscular, and/or other cell populations and to decrease activity in others. For example, relatively low frequency neurostimulation (i.e., less than about 50-100 Hz) typically has an excitatory effect on surrounding neural tissue, leading to increased neural activity, whereas relatively high frequency neurostimulation (i.e., greater than about 50-100 Hz) typically has an inhibitory effect, leading to decreased neural activity.

Similarly, excitatory neurotransmitters (e.g., acetylcholine), agonists thereof, and agents that act to increase levels of an excitatory neurotransmitter(s) (e.g., edrophonium) generally have an excitatory effect on neural tissue, while inhibitory neurotransmitters (e.g., gamma-aminobutyric acid, a.k.a. GABA), agonists thereof (e.g., benzodiazepines such as lorazepam and diazepam), and agents that act to increase levels of an inhibitory neurotransmitter(s) generally have an inhibitory effect. However, antagonists of inhibitory neurotransmitters (e.g., bicuculline) and agents that act to decrease levels of an inhibitory neurotransmitter(s) have been demonstrated to excite neural tissue, leading to increased neural activity.

In some preferred embodiments, stimulation of nerves and/or smooth muscle is advantageously used to modulate or direct the flow of anticoagulation medication. For example, stimulation of arteriolar smooth muscle tissue and/or the excitatory nerves innervating this tissue (sympathetic nerves) leads to a decrease of perfusion of the tissue fed by such arterioles due to a constriction in lumen area caused by contraction of the surrounding smooth muscle. Such a decrease in perfusion would allow a medication to remain in a tissue longer, if such medication were delivered to the tissues fed by constricted arterioles. Alternatively, such a decrease in perfusion may be used to selectively decrease delivery of a medication if the medication were delivered systemically and arterioles in a certain region were constricted. Relatively low frequency electrical stimulation (less than about 50-100 Hz) is likely to cause contraction of arteriolar smooth muscle, as are alpha-adrenoceptor agonists (e.g., phenylephrine, norepinephrine). Conversely, alpha-adrenoceptor antagonists (e.g., prazosin, terzosin, phentolamine) are likely to cause relaxation and dilation of vascular smooth muscle.

Some embodiments of stimulator 160 also include a power source and/or power storage device 166 (FIG. 3). Possible power options for a stimulation device of the present invention, described in more detail below, include but are not limited to an external power source coupled to the stimulation device (e.g., via an RF link), a self-contained power source utilizing any suitable means of generation or storage of energy (e.g., a primary battery, a replenishable or rechargeable battery such as a lithium ion battery, an electrolytic capacitor, a super- or ultra-capacitor, or the like), and if the self-contained power source is replenishable or rechargeable, means of replenishing or recharging the power source (e.g., an RF link, an optical link, a thermal link, or other energy-coupling link).

In embodiments such as depicted in FIG. 3, stimulator 160 includes a rechargeable battery as a power source/storage device 166. The battery is recharged, as required, from an external battery charging system (EBCS) 192, typically through an inductive link 194. In these embodiments, stimulator 160 includes a processor and other circuitry 154 that allow it to generate electrical/infusion pulses that are applied to a patient 208 through electrodes 172 and/or catheter(s) 180 in accordance with a program and stimulation parameters stored in programmable memory 164. As stated earlier, stimulation pulses of drugs include various types and/or rates of infusion, such as intermittent infusion, infusion at a constant rate, and bolus infusion.

According to certain embodiments, a stimulator operates independently. According to other embodiments, a stimulator operates in a coordinated manner with other stimulator(s), other implanted device(s), and/or other device(s) external to the patient's body. For instance, a stimulator may control or operate under the control of another implanted stimulator(s), other implanted device(s), and/or other device(s) external to the patient's body. A stimulator may communicate with other implanted stimulators, other implanted devices, and/or devices external to a patient's body via, e.g., an RF link, an ultrasonic link, a thermal link, and/or an optical link. Specifically, a stimulator may communicate with an external remote control (e.g., patient and/or clinician programmer) that is capable of sending commands and/or data to a stimulator and that may also be capable of receiving commands and/or data from a stimulator.

For example, in embodiments such as shown in FIG. 3, stimulator 160 may be activated and deactivated, programmed and tested through a hand held programmer (HHP) 200 (which may also be referred to as a patient programmer and is preferably, but not necessarily, hand held), a clinician programming system (CPS) 202 (which may also be hand held), and/or a manufacturing and diagnostic system (MDS) 204 (which may also be hand held). HHP 200 may be coupled to stimulator 160 via an RF link 195. Similarly, MDS 204 may be coupled to stimulator 160 via another RF link 196. In a like manner, CPS 202 may be coupled to HHP 200 via an infra-red link 197; and MDS 204 may be coupled to HHP 200 via another infra-red link 198. Telecommunicative links other than RF or infra-red may also be used for these purposes. Through these links, CPS 202, for example, may be coupled through HHP 200 to stimulator 160 for programming or diagnostic purposes. MDS 204 may also be coupled to stimulator 160, either directly through RF link 196, or indirectly through IR link 198, HHP 200, and RF link 195.

Figure 4:
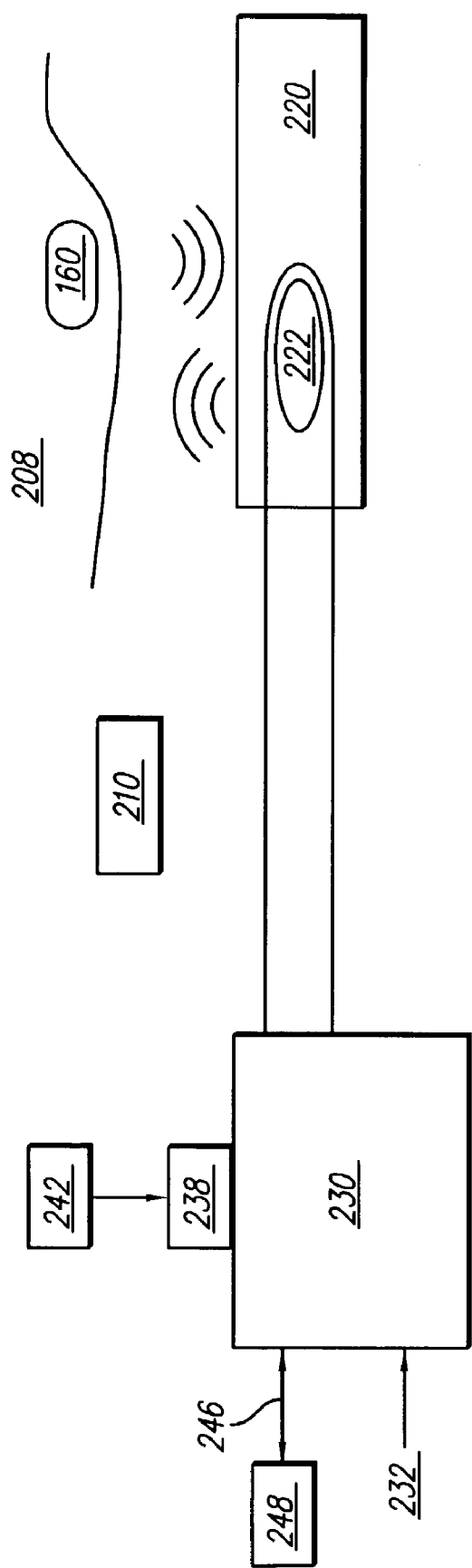
FIG. 4 illustrates an additional exemplary embodiment of external components of the invention.

In certain embodiments, and as illustrated in FIG. 4, the patient 208 may switch stimulator 160 on and off by use of controller 210, which may be handheld. Stimulator 160 is operated by controller 210 by any of various means, including sensing the proximity of a permanent magnet located in controller 210, sensing RF transmissions from controller 210, or the like.

Additional and alternative exemplary external components for programming and/or providing power to stimulator 160 are also illustrated in FIG. 4. When communication with stimulator 160 is desired, patient 208 is positioned on or near external appliance 220, which appliance contains one or more inductive coils 222 or other means of communication (e.g., RF transmitter and receiver). External appliance 220 is connected to or is a part of external circuitry appliance 230 which may receive power 232 from a conventional power source. External appliance 230 contains manual input means 238, e.g., a keypad, whereby the patient 208 or a caregiver 242 may request changes in the electrical and/or drug stimulation parameters produced during the normal operation of stimulator 160. In these embodiments, manual input means 238 include various electromechanical switches and/or visual display devices that provide the patient and/or caregiver with information about the status and prior programming of stimulator 160.

Alternatively or additionally, external appliance 230 is provided with an electronic interface means 246 for interacting with other computing means 248, such as by a serial interface cable or infrared link to a personal computer or to a telephone modem or the like. Such interface means 246 may permit a clinician to monitor the status of the implant and prescribe new stimulation parameters from a remote location.

One or more of the external appliance(s) may be embedded in a cushion, mattress cover, garment, or the like. Other possibilities exist, including a strap, patch, or other structure(s) that may be affixed to the patient's body or clothing. External appliances may include a package that can be, e.g., worn on the belt, may include an extension to a transmission coil affixed, e.g., with a VELCRO® band or an adhesive, or may be combinations of these or other structures able to perform the functions described herein.

To help determine the amount and/or type(s) of stimulating drug(s), and optionally, the strength and/or duration of electrical stimulation, required to produce the desired therapeutic effect, in some embodiments, a patient's response to and/or need for treatment is sensed. For instance, the electrical activity produced in response to stimulation may be detected, e.g., via recording of the associated electrocardiogram (ECG). When catheters and/or electrodes of a stimulator are implanted, for example, in and/or adjacent the left coronary artery or its branches, signals from an ECG sensor built into the stimulator may be used to adjust stimulation parameters. (As used herein, "adjacent" or "near" means as close as reasonably possible to target tissue(s), including touching or even being positioned within the tissue, but in general, may be as far as can be reached with the stimulation pulses). ECG and/or other sensing may be performed by an internal or external device. For instance, beat-to-beat T-wave variations, which are abnormal ECG events associated with an increased likelihood of ventricular arrhythmia, may be detected with measurement and comparisons of T-waves at a microvolt level (for instance, by the Heartwave™ System available from Cambridge Heart, Inc. of Bedford, Mass., which performs a Microvolt T-Wave Alternans™ Test).

Alternatively, a "stimulator" dedicated to sensory processes communicates with a stimulator that provides the electrical and/or infusion pulses. For instance, a microstimulator, such as a BION® manufactured by Advanced Bionics of Sylmar, Calif., may be used to detect abnormal cardiac electrocardiogram (ECG) changes/events. For instance, a BION may use one of many algorithms for analyzing ECGs. These algorithms can operate in the frequency domain, time domain or both. They may employ linear, non-linear, or statistical analysis to categorize the electrogram as originating from various modes, i.e., normal sinus rhythms, sinus tachycardia, ventricular tachycardia, and ventricular fibrillation. In addition, by finding the p, R, and T waves or analyzing the timing of the relationships and durations of the p-wave, QRS complex, and T-wave, it is possible to identify various abnormal events and disease states, and make predictive diagnosis about perfusion of the myocardium. See, for instance, U.S. Pat. No. 5,513,644, titled "Cardiac arrhythmia detection system for an implantable stimulation device," which is incorporated herein by reference in its entirety.

Alternatively or additionally, a "stimulator" (which may be a microstimulator, and which may or may not have "stimulating" means) may incorporate means of sensing the coagulation state of the patient, e.g., via Prothrombin Time (PT), International Normalized Ratio (INR), Partial Thromboplastin Time (PTT), Specific Prothrombin (Factor II) Assay, Native Prothrombin Antigen Assay, and/or Anti-Xa Assay. In other examples, a microstimulator(s) may sense EEG changes/events, or other indicator(s) of myocardial infarction, stroke, pulmonary embolism, deep vein thrombosis, and/or symptoms thereof. Alternatively or additionally, a "stimulator" may incorporate means of sensing thromboembolic disease, cardiac ischemia, cerebral ischemia, and/or pulmonary ischemia, limb ischemia, e.g., via an oxygen sensor or a flow sensor in one or more of these tissues. For instance, a microstimulator(s) may sense Troponin-I or Troponin-T, which are marker of ischemia. See, for instance, U.S. Pat. No. 5,753,517, titled "Quantitative immunochromatographic assays," which is incorporated herein by reference in its entirety. Antibodies that bind to Troponin-I may be sensed, for instance, with a detection reagent (to which the antibodies bind) and measured using electrical conductivity or capacitance. A microstimulator or other sensor could additionally or alternatively measure an antibody that fluoresces when binding to Troponin-I, for instance, with an LED encased in a hermetic glass seal coated with the antibody.

As described below, implant circuitry 154 may, if necessary, amplify and transmit these sensed signals, which may be analog or digital. A stimulator may incorporate other means of sensing in order to determine the required stimulation, including sensing levels or changes of any blood borne substance, including medications, hormones, or other substances, such as D-dimers, and/or other methods mentioned herein, and yet others evident to those of skill in the art upon review of the present disclosure. For instance, one or more Chemically Sensitive Field-Effect Transistors (CHEMFETs), such as Enzyme-Selective Field-Effect Transistors (ENFETs) or Ion-Sensitive Field-Effect Transistors (ISFETs, as are available from Sentron CMT of Enschede, The Netherlands), may be used. The sensed information may be used to control stimulation parameters in a closed-loop manner.

Therefore, in several embodiments, a first and second "stimulator" are provided. The second "stimulator" periodically (e.g., once per minute) senses, for example, the level of heparin in the circulatory system via an anti-Xa assay, and transmits this information to the first stimulator. The first stimulator uses the sensed information to adjust drug and/or electrical stimulation parameters according to an algorithm programmed, e.g., by a clinician. For example, the infusion rate of an anticoagulant, such as heparin may be increased in response to decreased anti-Xa activity. In some alternatives, one stimulator performs both the sensing and stimulating functions.

While a stimulator may also incorporate means of sensing thromboembolic disease, cardiac ischemia, cerebral ischemia, pulmonary ischemia, myocardial infarction, stroke, pulmonary embolism, deep vein thrombosis, the coagulation state of a patient, and/or symptoms of any of these, it may alternatively or additionally be desirable to use a separate or specialized implantable device to record and telemeter physiological conditions/responses in order to adjust electrical stimulation and/or drug infusion parameters. This information may be transmitted to an external device, such as external appliance 220, or may be transmitted directly to implanted stimulator(s) 160. However, in some cases, it may not be necessary or desirable to include a sensing function or device, in which case stimulation parameters are determined and refined, for instance, by patient feedback, or the like.

Thus, it is seen that in accordance with the present invention, one or more external appliances may be provided to interact with stimulator(s) 160, and may be used to accomplish, potentially among other things, one or more of the following functions:

Function 1: If necessary, transmit electrical power from the external electronic appliance 230 via appliance 220 to stimulator 160 in order to power the device and/or recharge the power source/storage device 166. External electronic appliance 230 may include an automatic algorithm that adjusts drug and/or electrical stimulation parameters automatically whenever the stimulator(s) 160 is/are recharged.

Function 2: Transmit data from the external appliance 230 via the external appliance 220 to stimulator 160 in order to change the parameters of drug and/or electrical stimulation used by stimulator 160.

Function 3: Transmit sensed data indicating a need for treatment or in response to stimulation from stimulator 160 to external appliance 230 via external appliance 220.

Function 4: Transmit data indicating state of the stimulator 160 (e.g., battery level, drug level, electrical stimulation and/or infusion settings, etc.) to external appliance 230 via external appliance 220.

By way of example, referring for example to FIG. 4, a treatment modality for thromboembolic disease may be carried out according to the following procedure:

1. A stimulator 160 is implanted so that its catheter discharge portion 182 and one or more electrodes 172 are located in the coronary arteries, sinus, and/or veins. If necessary or desired, additional leads 170' and/or catheters 180' may be used so that, for example, electrodes 172' and/or catheter discharge portions(s) 182' may additionally or alternatively be located in or adjacent atria, ventricles, blood vessels, or on the surface of the myocardium.
2. Using Function 2 described above (i.e., transmitting data) of external electronic appliance 230 and external appliance 220, the stimulator 160 is commanded to infuse amounts of heparin, possibly while producing a series of excitatory electrical stimulation pulses.
3. After each electrical/infusion pulse, series of stimulation pulses, or at some other predefined interval, any change in, e.g., anti-Xa activity or activated partial thromboplastin time (APTT) resulting from the stimulation is sensed, for instance, by one or more electrodes 172 and/or 172' acting as sensors. If necessary, these responses are converted to data and telemetered out to external electronic appliance 230 via Function 3.
4. From the response data received at external appliance 230, or from other assessment, the stimulus threshold for obtaining a response is determined and is used by a clinician 242 acting directly 238 or by other computing means 248 to transmit the desired electrical and/or drug stimulation parameters to stimulator 160 in accordance with Function 2. Alternatively, external appliance 230 makes the proper adjustments automatically, and transmits the proper stimulation parameters to stimulator 160. In yet another alternative, stimulator 160 adjusts stimulation parameters automatically based on the sensed response.
5. When patient 208 desires to invoke electrical stimulation and/or drug infusion, patient 208 employs controller 210 to set stimulator 160 in a state where it delivers a prescribed stimulation pattern from a predetermined range of allowable stimulation patterns.
6. Patient 208 employs controller 210 to turn off stimulator 160, if desired.
7. Periodically, the patient or caregiver recharges the power source/storage device 166 of stimulator 160, if necessary, in accordance with Function 1 described above (i.e., transmit electrical power).

For the treatment of any of the various types and severities of thromboembolic disease, symptoms thereof, and/or various coagulation states of patients, it may be desirable to modify or adjust the algorithmic functions performed by the implanted and/or external components, as well as the surgical approaches, in ways that would be obvious to skilled practitioners of these arts. For example, in some situations, it may be desirable to employ more than one stimulator 160, each of which could be separately controlled by means of a digital address. Multiple channels and/or multiple patterns of drug and/or electrical stimulation might thereby be programmed by the clinician and controlled by the patient in order to, for instance, deal with complex or multiple symptoms or conditions, such as may result from complex diseases, e.g., lupus, or as a result of a combination of disorders, e.g., atherosclerosis and protein S deficiency.

Various embodiments of the present invention use one or more anticoagulation drugs to treat and/or prevent thromboembolic disease chronically. According to such embodiments, one or more of the infused drugs is a medication used for chronic treatment of thromboembolic disease, such as heparin, low molecular weight heparin, warfarin, aspirin, or any platelet aggregation inhibitor, such as clopidogrel and ticlopidine. Such chronic medication may be delivered at a basal rate or via periodic bolus, as programmed by a clinician. The dosage may also be programmed with other drug delivery algorithms by a clinician. Once again, sensing capabilities described earlier may be used for adjustments to chronic treatment. For example, the infusion rate of low molecular weight heparin may be modulated by a sensor that senses partial thromboplastin time (PTT) or anti-Xa assay.

Some embodiments of the present invention use one or more drugs to deliver thromboembolic therapy acutely. According to such embodiments, one or more of the infused drugs is a medication used for acute treatment of thromboembolic disease, such as streptokinase or its derivatives, plasminogen activator or its derivatives, and/or urokinase or its derivatives. Such acute medication may be delivered on demand when the patient indicates such delivery is required, such as via depression of an implanted button or via a remote control that is in communication with the stimulator. The control algorithm and/or dosage may also be programmed by a clinician. If the stimulator has sensing capability, as discussed earlier, such acute medication may alternatively be delivered on demand when the stimulator senses a change in perfusion of a certain area, as programmed by a clinician. For example, tPA might be delivered by the stimulator when it senses T wave inversion and ST elevation on the ECG (abnormal ECG events, as known by those of skill in the art).

Certain embodiments of the present invention use one or more drugs to deliver anticoagulation therapy acutely. According to such embodiments, one or more of the infused drugs is a medication used for acute treatment of a pathological thrombus (e.g., due to underlying thromboembolic disease), such as heparin or low molecular weight heparin or a thrombus-dissolving medication such as urokinase or tissue plasminogen activator (tPA, a.k.a., alteplase). Such acute medication may be delivered on demand when the patient indicates such delivery is required, such as via depression of an implanted button or via a remote control in communication with the stimulator. The control algorithm and/or dosage may also be programmed by a clinician. Again, if the stimulator has sensing capability, as discussed earlier, such acute medication may alternatively be delivered when the stimulator senses a change in perfusion of a certain area, as programmed by a clinician. For example, heparin might be delivered by the stimulator when it senses T wave inversion and ST elevation (i.e., abnormal events) on the ECG.

Some forms of the present invention use more than one, even all, of the approaches mentioned above. As such, some combination of drug(s) to treat thromboembolic disease chronically and acutely, and to provide anticoagulation and thrombus dissolution therapy acutely may provide the best treatment to some patients. Once again, sensing capabilities described earlier may be used for adjustments to and timing of these treatments.

The drugs and other substances described above may be delivered via approaches, systems, and methods described earlier to one or more of the coronary arteries 100, one or more of the coronary veins 102, the aorta 104, the left ventricle 108, the left atrium 112, one or more of the pulmonary veins 116, the coronary sinus 120, any of the carotid arteries 122, any of the anterior, middle, or posterior cerebral arteries 124, the circle of Willis 128, any meningeal arteries (not shown), the basilar artery 134, any of the pulmonary arteries 138, the superior vena cava 140, the inferior vena cava 142, the right atrium 144, the right ventricle 146, any of the deep veins of the leg, any vessel that may influence cerebral circulation, any vessel that may influence pulmonary circulation, any vessel that may influence circulation in the lower limbs, and/or any other blood vessel or other location mentioned herein. As discussed earlier, electrical stimulation may also be applied during infusion of one or more stimulating drugs.

Furthermore, sensing means described earlier may be used to coordinate the subacute and/or chronic treatment of thromboembolic disease and related morbidities by infusion and optional electrical stimulation, and then, when appropriate, the acute treatment of thromboembolic disease symptoms, e.g., acute thrombus formation leading to sudden ischemia, as in a stroke. Alternatively, this coordination may be programmed, and not based on a sensed condition. In yet another alternative, this coordination may be controlled by the patient via the patient programmer.

While the invention herein disclosed has been described by means of specific embodiments and applications thereof, numerous modifications and variations could be made thereto by those skilled in the art without departing from the scope of the invention set forth in the claims.

What is claimed is:

1. A method for directing flow of anticoagulation medication, the method comprising:
    delivering at least one of a thrombolytic drug and an anticoagulation drug to a first tissue via an implanted treatment device that includes
        a catheter having a discharge portion positioned to deliver the at least one drug to the first tissue, and
        a lead having a stimulating electrode positioned to deliver an electrical pulse to a second tissue; and
    limiting perfusion of the first tissue by delivering the electrical pulse to the second tissue via the stimulating electrode, wherein the electrical pulse is configured to constrict at least one arteriole supplying the first tissue.

2. The method of claim 1, wherein delivering the electrical pulse to the second tissue comprises delivering the electrical pulse to at least one of nerve tissue and/or smooth muscle tissue.

3. The method of claim 1, wherein the first tissue comprises at least one of a coronary artery, a coronary vein, the coronary sinus, the left ventricle, the left atrium, the surface of the myocardium, a pulmonary vein, a carotid artery, the anterior cerebral artery, the middle cerebral artery, the posterior cerebral artery, the circle of Willis, a meningeal artery, the basilar artery, a pulmonary artery, the superior vena cava, the inferior vena cava, the right ventricle, the right atrium, the aorta, a common iliac vessel, an internal iliac vessel, an external iliac vessel, a femoral vessel, a renal vessel, the celiac trunk, the middle colic artery, a superior mesenteric vessel, an inferior mesenteric vessel, a deep vein of the leg, a vessel that influences coronary circulation, a vessel that influences cerebral circulation, a vessel that influences pulmonary circulation, a vessel that influences circulation of the lower limbs, and a vessel that influences visceral circulation.

4. The method of claim 1, wherein the electrical pulse is configured to constrict the at least one arteriole by causing contraction of smooth muscle surrounding at least one arteriole.

5. A method for providing at least one of thrombolytic or anticoagulation therapy, comprising:
    providing a stimulator that generates a pulse in accordance with prescribed parameters;
    providing a catheter connected to the stimulator, which catheter includes a discharge portion;
    providing a lead connected to the stimulator, the lead including at least one electrode;
    implanting the catheter discharge portion adjacent to at least one tissue;
    implanting the stimulator at a location remote from the at least one tissue to be stimulated;
    implanting the lead adjacent to at least a second one tissue;
    delivering, via the catheter, pulses of at least one drug as at least one of thrombolytic or anticoagulation treatment to at least one tissue, which tissue comprises at least one of a coronary artery, a coronary vein, the coronary sinus, the left ventricle, the left atrium, the surface of the myocardium, a pulmonary vein, a carotid artery, the anterior cerebral artery, the middle cerebral artery, the posterior cerebral artery, the circle of Willis, a meningeal artery, the basilar artery, a pulmonary artery, the superior vena cava, the inferior vena cava, the right ventricle, the right atrium, the aorta, a common iliac vessel, an internal iliac vessel, an external iliac vessel, a femoral vessel, a renal vessel, the celiac trunk, the middle colic artery, a superior mesenteric vessel, an inferior mesenteric vessel, a deep vein of the leg, a vessel that influences coronary circulation, a vessel that influences cerebral circulation, a vessel that influences pulmonary circulation, a vessel that influences circulation of the lower limbs, and a vessel that influences visceral circulation; and
    limiting perfusion of the at least one tissue by delivering, via the lead, an electrical stimulating pulse to the at least one tissue, wherein said electrical pulse is configured to constrict at least one arteriole supplying the at least one tissue.

6. The method of claim 5 further comprising providing at least one sensor to sense at least one physical condition, and adjusting the parameters based on the at least one sensed condition.

7. A method for providing at least one of thrombolytic or anticoagulation therapy, comprising:
    providing a stimulator that includes a lead having at least one electrode to generate a pulse in accordance with prescribed parameters;
    providing a catheter connected to the stimulator, which catheter includes a discharge portion;
    implanting the catheter discharge portion adjacent to at least one tissue to be stimulated;
    implanting the stimulator at a location remote from the at least one tissue to be stimulated;
    chronically delivering via the catheter at least one drug as at least one of thrombolytic or anticoagulation treatment to at least one tissue;
    increasing delivery via the catheter of at least one drug to the at least one tissue during an acute emergency, which tissue comprises at least one of a coronary artery, a coronary vein, the coronary sinus, the left ventricle, the left atrium, the surface of the myocardium, a pulmonary vein, a carotid artery, the anterior cerebral artery, the middle cerebral artery, the posterior cerebral artery, the circle of Willis, a meningeal artery, the basilar artery, a pulmonary artery, the superior vena cava, the inferior vena cava, the right ventricle, the right atrium, the aorta, a common iliac vessel, an internal iliac vessel, an external iliac vessel, a femoral vessel, a renal vessel, the celiac trunk, the middle colic artery, a superior mesenteric vessel, an inferior mesenteric vessel, a deep vein of the leg, a vessel that influences coronary circulation, a vessel that influences cerebral circulation, a vessel that influences pulmonary circulation, a vessel that influences circulation of the lower limbs, and a vessel that influences visceral circulation; and limiting perfusion of the at least one tissue by delivering an electrical pulse to the at least one tissue, wherein said electrical pulse is configured to constrict at least one arteriole supplying the at least one tissue.

8. The method of claim 7 wherein the electrical pulse is configured to constrict the at least one arteriole by causing contraction of smooth muscle surrounding the at least one arteriole.

9. The method of claim 7 wherein the limiting of the perfusion of the at least one tissue is configured to increase an amount of time that the at least one drug remains in the at least one tissue.

10. The method of claim 7 wherein the at least one drug comprises at least one anticoagulant.

11. The method of claim 7 wherein the at least one drug delivered during the acute emergency comprises at least one thromboembolytic drug.

12. The method of claim 7 wherein the at least one drug comprises at least one of heparin, low molecular weight heparin, warfarin, aspirin, a platelet aggregation inhibitor, streptokinase, a streptokinase derivative, a tissue plasminogen activator (tPA), a plasminogen activator derivative, anistreplase, urokinase, and a urokinase derivative.

13. The method according to claim 7 wherein the at least one drug that is chronically delivered provides chronic treatment delivered at a basal rate or via periodic bolus of at least one of heparin, low molecular weight heparin, warfarin, aspirin, and a platelet aggregation inhibitor.

14. The method according to claim 7 wherein the at least one drug delivered during the acute emergency comprises at least one of streptokinase, a streptokinase derivative, a tissue plasminogen activator (tPA), a plasminogen activator derivative, urokinase, a urokinase derivative, anistreplase, heparin, and low molecular weight heparin.

15. The method according to claim 7 further comprising providing both acute treatment and chronic treatment with a same at least one drug.

16. The method of claim 7 further comprising providing at least one sensor to sense at least one physical condition, and adjusting the parameters based on the at least one sensed condition.

17. The method of claim 16 wherein the at least one sensed condition is at least anticoagulation status.

18. The method of claim 16 wherein the at least on sensed condition is at least one of an abnormal ECG event, an abnormal EEG event, an abnormal ultrasound echocardiogram event, oxygen level, flow level, change in perfusion, coagulation state, left ventricular end diastolic pressure, pulmonary capillary wedge pressure, systemic blood pressure, cardiac output, Prothrombin Time (PT), International Normalized Ratio (INR), Partial Thromboplastin Time (PTT), Activated Partial Thromboplastin Time (APTT), Native Prothrombin Antigen Assay, Specific Prothrombin Assay, Anti-Xa Assay, medication level, hormone level, D-dimer level, lupus anticoagulant antibody level, anti-cardiolipin antibody level, Troponin-1 level, Troponin-T level, and level of antibodies that bind to Troponin-1.

19. The method of claim 16 wherein the at least one sensed condition is an indicator of at least one of myocardial infarction, stroke, cardiomyopathy, pulmonary embolism, paradoxical embolism, venous thrombosis, deep vein thrombosis, clotted arteriovenous fistula or shunt, atrial fibrillation, thrombus, thromboembolic disease, cardiac ischemia, cerebral ischemia, pulmonary ischemia, limb ischemia, and mesenteric ischemia.

20. The method of claim 16 wherein the at least one sensor comprises at least one of an internal device and an external device.

21. An implantable system for providing at least one of thrombolytic or anticoagulation therapy, the system comprising:
a power storage device;
a stimulating electrode positionable to deliver an electrical pulse to a tissue;
a memory storing stimulation parameters that describe an electrical pulse operable to modulate an arteriole lumen area of an arteriole by exciting activity in a neural or a muscular cell;
an electrical signal generator to receive the stimulation parameters from the memory and to generate the electrical pulse deliverable by the stimulating electrode in accordance with the stimulation parameters, the electrical pulse generated using power drawn from the power storage device;
means for chronically delivering a first drug for the thrombolytic or anticoagulation therapy to at least one tissue in accordance with prescribed parameters, the at least one tissue comprising at least one of a coronary artery, a coronary vein, the coronary sinus, the left ventricle, the left atrium, the surface of the myocardium, a pulmonary vein, a carotid artery, the anterior cerebral artery, the middle cerebral artery, the posterior cerebral artery, the circle of Willis, a meningeal artery, the basilar artery, a pulmonary artery, the superior vena cava, the inferior vena cava, the right ventricle, the right atrium, the aorta, a common iliac vessel, an internal iliac vessel, an external iliac vessel, a femoral vessel, a renal vessel, the celiac trunk, the middle colic artery, a superior mesenteric vessel, an inferior mesenteric vessel, a deep vein of the leg, a vessel that influences coronary circulation, a vessel that influences cerebral circulation, a vessel that influences pulmonary circulation, a vessel that influences circulation of the lower limbs, and a vessel that influences visceral circulation; and
means for acutely delivering a second drug for the thrombolytic or anticoagulation therapy to the at least one tissue.

22. The system of claim 21 further comprising means for providing the prescribed parameters to the drug discharge device.

23. The system of claim 22 wherein the means for providing the prescribed parameters comprises a physiological condition sensor.

24. The system of claim 22 wherein the system further comprises:
an implantable physiological condition sensor to sense at least one physiological condition indicative of an acute emergency and to generate a signal indicative of the acute emergency; and
a controller to increase the delivery of the second drug for the thrombolytic or anticoagulation therapy in response to a receipt of the signal indicative of the acute emergency.

* * * * *